United States Patent [19]

Costa et al.

[11] Patent Number: 5,474,539
[45] Date of Patent: Dec. 12, 1995

[54] TROCAR WITH RETRACTING TIP

[75] Inventors: Peter F. Costa, Winthrop; William A. Holmes, Marblehead, both of Mass.; Frederic H. Moll, San Francisco, Calif.

[73] Assignee: Origin Medsystems, Inc., Menlo Park, Calif.

[21] Appl. No.: 15,349

[22] Filed: Feb. 8, 1993

Related U.S. Application Data

[63] Continuation-in-part of Ser. No. 752,838, Aug. 30, 1991, abandoned, and a continuation-in-part of Ser. No. 7,368, Jan. 21, 1993, abandoned, which is a continuation of Ser. No. 754,051, Aug. 30, 1991, abandoned, said Ser. No. 752,838, is a continuation-in-part of Ser. No. 651,756, Feb. 7, 1991, abandoned.

[51] Int. Cl.[6] .................................................. A61M 5/178
[52] U.S. Cl. .......................................... 604/164; 604/167
[58] Field of Search .......................... 604/110, 164–170, 604/256, 263, 264, 272, 274, 283, 117, 31, 46, 51; 606/181–185; 128/753, 754

[56] References Cited

U.S. PATENT DOCUMENTS

| | | | |
|---|---|---|---|
| 1,248,492 | 12/1917 | Hill . | |
| 2,001,638 | 11/1932 | Tornsjo | 128/347 |
| 2,623,521 | 12/1952 | Shaw | 128/221 |
| 2,630,803 | 3/1953 | Baran | 128/221 |
| 3,713,447 | 1/1973 | Adair | 128/347 |
| 3,994,287 | 11/1976 | Turp et al. | 128/6 |
| 4,254,762 | 3/1981 | Yoon | 128/4 |
| 4,256,119 | 3/1981 | Gauthier | 128/754 |
| 4,442,836 | 4/1984 | Meinecke et al. | 128/314 |
| 4,449,529 | 5/1984 | Burns et al. | 128/314 |
| 4,499,898 | 2/1985 | Knepshield et al. | 128/305 |
| 4,517,978 | 5/1985 | Levin et al. | 128/314 |

(List continued on next page.)

FOREIGN PATENT DOCUMENTS

| | | | |
|---|---|---|---|
| 0293123A2 | 11/1988 | European Pat. Off. | A61B 17/11 |
| 0312219A2 | 4/1989 | European Pat. Off. | A61B 17/34 |
| 0349955A1 | 1/1990 | European Pat. Off. | A61B 17/34 |
| 0350291A2 | 1/1990 | European Pat. Off. | A61B 17/34 |
| 0370733A3 | 5/1990 | European Pat. Off. | A61B 17/34 |
| 0378095A1 | 7/1990 | European Pat. Off. | A61B 17/34 |
| 0413493A3 | 2/1991 | European Pat. Off. | A61B 17/34 |
| 0430594A1 | 6/1991 | European Pat. Off. | A61B 17/34 |
| 0432363A3 | 6/1991 | European Pat. Off. | A61B 17/34 |

(List continued on next page.)

OTHER PUBLICATIONS

Zubairov, "Needle for the Puncture and Lavage of the Abdominal Cavity," Traumatology Clinic, Novokuznetsk Institute of Advanced Medical Studies (w/translation).
Amended Complaint, *U.S. Surgical v. Origin Medsystems*, U.S. District Court, N. D. Calif., Case No. C 92–1892 VRW.
Roth, "Alternative Safety Trocar," Nov. 6, 1985.
Endotherapeutics, Trocar Drawings, 1–2186.
Roth, Communication to James Peterson with attachment regarding Trocar, Feb. 26, 1992.
Order Granting Preliminary Injunction, U.S. District Court, N.D. Calif., Jan. 12, 1993.

*Primary Examiner*—C. Fred Rosenbaum
*Assistant Examiner*—Mark Bockelman
*Attorney, Agent, or Firm*—Limbach & Limbach

[57] ABSTRACT

A trocar assembly consisting of a trocar tube subassembly and a separate interengageable trocar body subassembly is provided. The trocar body subassembly includes an elongated obturator having a sharp pointed tip which is normally housed within an elongated tube of the trocar tube subassembly. The obturator is extendable from a retracted position within the tube wherein the tip is recessed from the tube end to an operative position forward of said tube end and outside the tube. By manually advancing the trocar assembly against a body wall, the resisting force locks the obturator in the operative position. Relaxation of the force incident to passing through the body wall causes the obturator to be automatically unlocked and retracted to its initial position with the tip positioned protectively within the tube, thereby protecting body tissues and organs from being damaged by the tip when it enters a body cavity beyond the wall.

8 Claims, 12 Drawing Sheets

U.S. PATENT DOCUMENTS

| | | | |
|---|---|---|---|
| 4,527,561 | 7/1985 | Burns | 606/182 |
| 4,535,773 | 8/1985 | Yoon | 604/169 |
| 4,559,041 | 12/1985 | Razi | 604/157 |
| 4,601,710 | 7/1986 | Moll | 604/165 |
| 4,654,030 | 3/1987 | Moll et al. | 604/165 |
| 4,747,831 | 3/1988 | Kulli | 604/110 |
| 4,766,907 | 8/1988 | de Groot et al. | 128/754 |
| 4,793,363 | 12/1988 | Ausherman et al. | 128/754 |
| 4,808,168 | 2/1989 | Warring | 604/158 |
| 4,813,426 | 3/1989 | Haber et al. | 128/763 |
| 4,817,631 | 4/1989 | Schnepp-Pesch et al. | 128/753 |
| 4,850,961 | 7/1989 | Wanderer et al. | 604/53 |
| 4,869,717 | 9/1989 | Adair | 604/164 |
| 4,895,147 | 1/1990 | Bodicky et al. | 606/182 |
| 4,902,280 | 2/1990 | Lander | 604/165 |
| 4,931,042 | 6/1990 | Holmes et al. | 604/164 |
| 4,943,280 | 7/1990 | Lander | 604/169 |
| 4,973,313 | 11/1990 | Katsaros et al. | 604/165 |
| 4,973,316 | 11/1990 | Dysarz | 604/195 |
| 5,009,643 | 4/1991 | Reich et al. | 604/165 |
| 5,030,206 | 7/1991 | Lander | 604/164 |
| 5,046,508 | 9/1991 | Weissler | 128/763 |
| 5,053,016 | 10/1991 | Lander | 604/169 |
| 5,057,082 | 10/1991 | Burchette, Jr. | 604/164 |
| 5,066,288 | 11/1991 | Deniega et al. | 604/274 |
| 5,092,853 | 3/1992 | Couvertier, II | 604/195 |
| 5,098,388 | 3/1992 | Kulkashi et al. | 604/164 |
| 5,104,382 | 4/1992 | Brinkerhoff et al. | 604/165 |
| 5,114,407 | 5/1992 | Burbank | 604/164 |
| 5,116,353 | 5/1992 | Green | 604/164 |
| 5,127,909 | 7/1992 | Shichman | 604/165 |
| 5,152,754 | 10/1992 | Plyley et al. | 604/164 |
| 5,158,552 | 10/1992 | Borgia et al. | 604/165 |
| 5,196,025 | 3/1993 | Ranalletta et al. | 606/185 |
| 5,224,470 | 7/1993 | Schnepp-Pesch et al. | 128/754 |
| 5,224,952 | 7/1993 | Deniega et al. | 604/164 |
| 5,226,426 | 7/1993 | Yoon | 604/164 |
| 5,295,993 | 3/1994 | Green | 604/160 |
| 5,318,580 | 6/1994 | Gresl, Jr. | 606/185 |

FOREIGN PATENT DOCUMENTS

| | | | |
|---|---|---|---|
| 0433581A3 | 6/1991 | European Pat. Off. | A61B 17/34 |
| 0450886A1 | 10/1991 | European Pat. Off. | A61M 1/00 |
| 0450111A1 | 10/1991 | European Pat. Off. | A61B 1/06 |
| 0461568A1 | 12/1991 | European Pat. Off. | A61B 17/34 |
| 3915597C1 | 5/1990 | Germany | A61B 1/00 |
| 3918431C1 | 7/1990 | Germany | A61M 19/00 |
| 4002235A1 | 8/1990 | Germany | A61B 1/00 |
| 3915215A1 | 11/1990 | Germany | A61B 17/34 |
| 3923243A1 | 1/1991 | Germany | A61B 17/34 |
| 4020956A1 | 1/1991 | Germany | A61B 17/34 |
| 475215 | 10/1952 | Spain . | |
| 921554 | 4/1982 | U.S.S.R. | A61B 17/34 |
| 2240926 | 8/1991 | United Kingdom | A61M 29/00 |
| WO89/03661 | 5/1989 | WIPO | A61B 17/34 |
| WO91/08712 | 6/1991 | WIPO | A61B 17/34 |

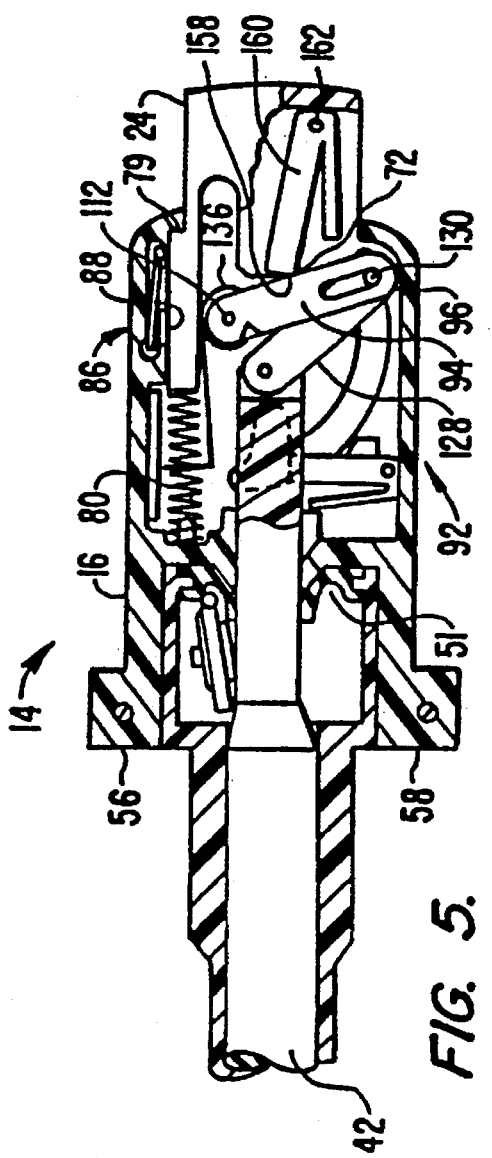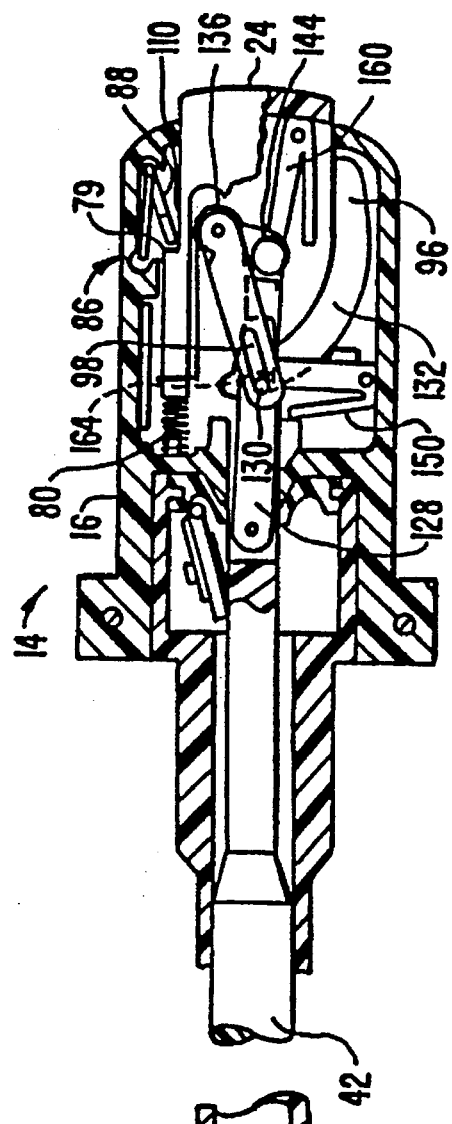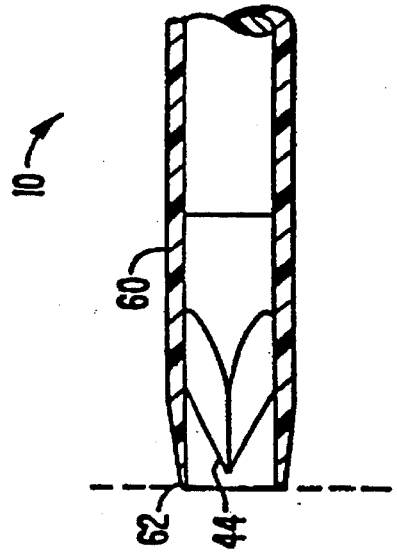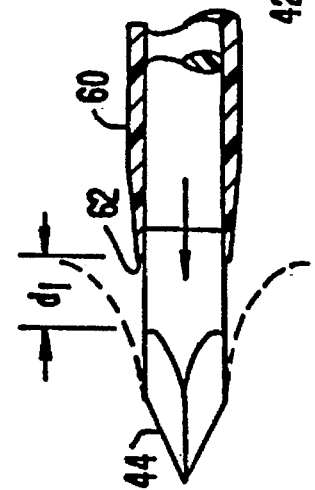
FIG. 5.
FIG. 6.

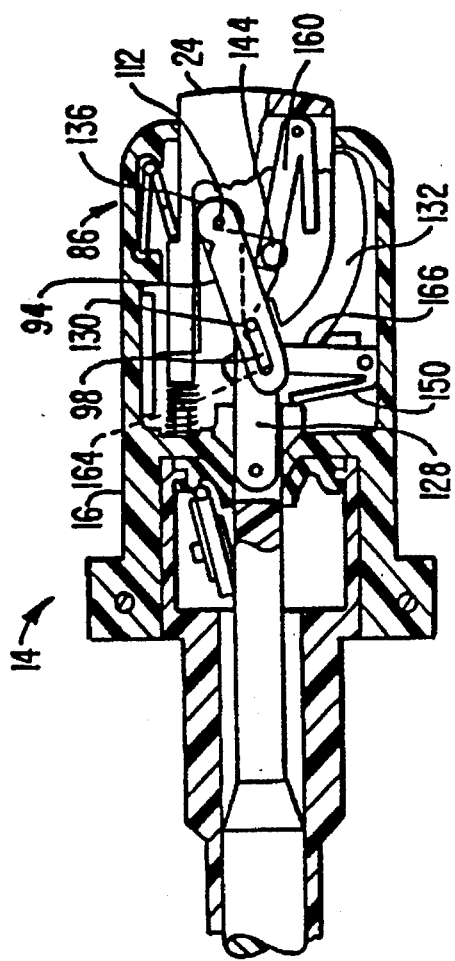
FIG. 7.
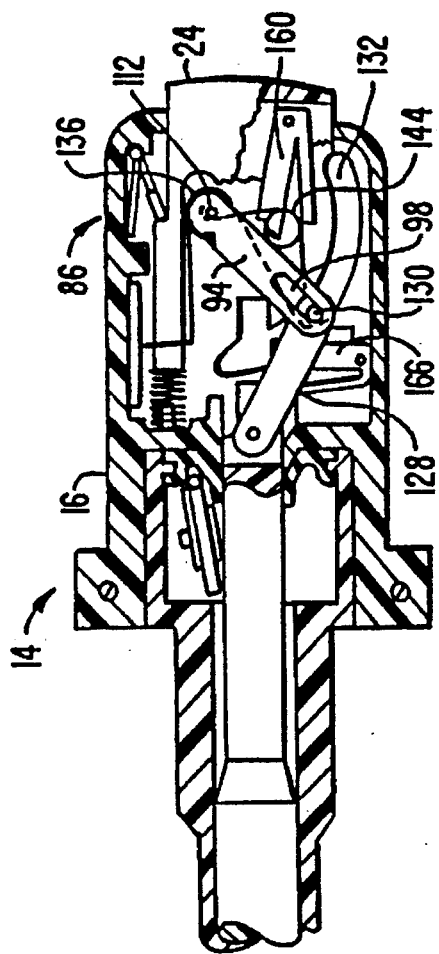
FIG. 8.
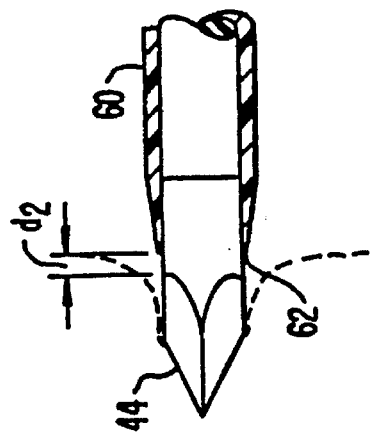
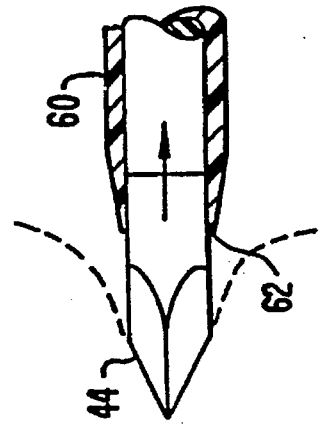

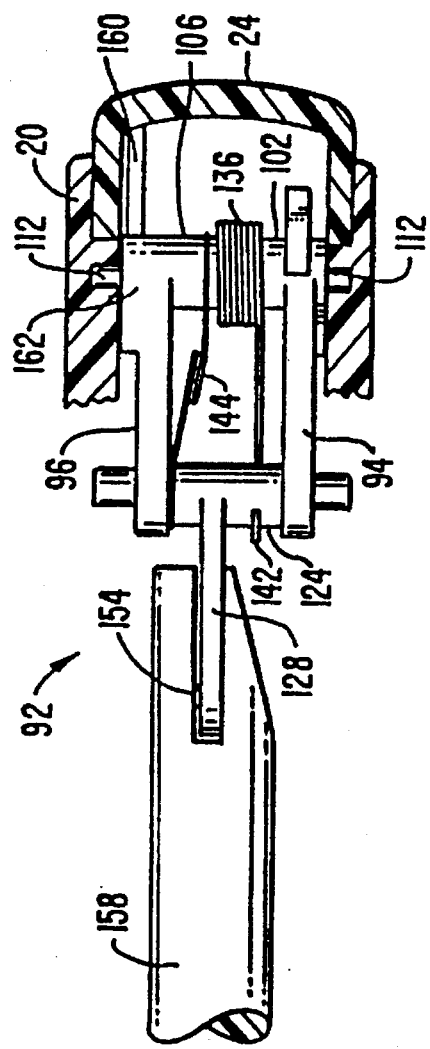
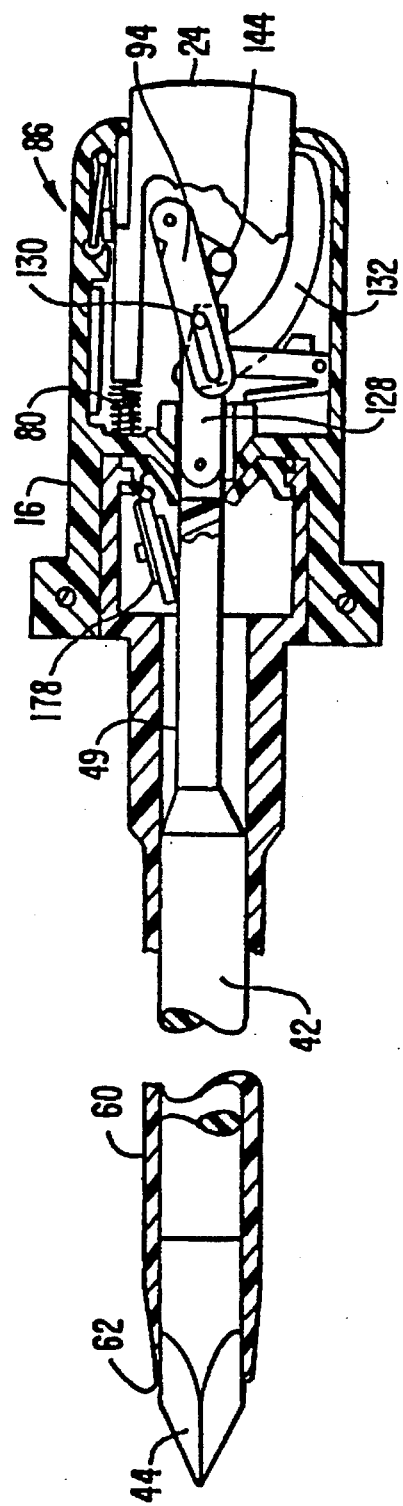
FIG. 9.
FIG. 10.

TROCAR WITH RETRACTING TIP

RELATED APPLICATIONS

This application is a continuation-in-part of application Ser. No. 752,838 filed Aug. 30, 1991, now abandoned, which is a continuation-in-part of application Ser. No. 651,756 filed Feb. 7, 1991, now abandoned. This application is also a continuation-in-part of application Ser. No. 08/007,368 filed Jan. 21, 1993, now abandoned, which is a file-wrapper continuation of application Ser. No. 754,051, filed Aug. 30, 1991, now abandoned.

BACKGROUND OF THE INVENTION

1. Field of the Invention

This invention relates to surgical instruments, and in particular to an improved trocar for providing communication with a body cavity.

2. Description of the Relevant Art

Trocars are very useful surgical instruments that essentially comprise a trocar tube or cannula, which surrounds an obturator (styler) having a sharp point tip or tip on the distal end thereof. The trocar assembly thus described is manually forced by the surgeon with the sharp point or tip serving to pierce the body wall so as to admit the surrounding trocar tube. After the tube is in communication with the body cavity, the obturator is removed and various instruments may be inserted into the cavity through the trocar tube. One such application is to insert an endoscopic instrument for performing endoscopic surgery within the cavity.

A common problem with early trocars was the danger associated with an unprotected piercing tip of the obturator. Being very sharp, the tip can cause injury to the surgeon if unprotected prior to use. During use, the obturator and trocar tube are forcibly thrust through a body wall until the tube is within the body cavity, so as to provide access thereto from the body exterior. After performing its function of piercing the body wall to admit the tube, the sharp tip may cause damage to body tissue and organs within the cavity.

In order to solve these and other problems, trocars have been developed that have spring-loaded tubular shields that normally protect and cover the sharp pointed tip until and incident to the trocar tube being thrust through the body wall tissue. Two such prior art trocars are shown in U.S. Pat. No. 4,601,710 to Moll and U.S. Pat. No. 4,654,030 to Moll, et al. With the devices of these patents, the surrounding trocar tube is forced in a proximal direction against a biasing spring incident to passing through the body wall tissue so as to expose the pointed tip, which is normally recessed just inside the open distal end of the trocar tube. Once through the body wall, the force on the trocar tube diminishes and it is forced in a distal direction by spring force until it again covers the tip. It thus covers the sharp pointed tip within the body cavity and thereby protects against injury. A locking mechanism may also be provided so that the trocar tube may not be accidentally retracted.

A problem with this just-described prior art device is that the trocar tube must move distally against tissue resistance in order to cover and protect the tip within the body cavity. Another problem is that a fairly high penetration force is required.

SUMMARY OF THE INVENTION

In order to solve the above-described problems, the instant invention provides a trocar wherein an obturator within the trocar tube is movable from a protected position within the tube to an advanced or operative position in advance of the distal end of the tube. After piercing the body wall and entering the cavity, a mechanism in the trocar body reacts to a decrease in force on the tip, and the obturator and attached tip are quickly and automatically withdrawn to a retracted position within the protective trocar tube.

In one embodiment, a cocking mechanism is provided that is actuable by one hand by means of a palm-operated pushbutton in the rear of the grip housing. By depressing the pushbutton with the palm of the hand, the point is moved forward to be in advance of the trocar tube, and the pushbutton is locked in the depressed position. A mechanical advantage or motion amplification is provided wherein the movement of the pushbutton results in about a 2:1 movement of the obturator. In other words, the obturator moves about twice the distance as the pushbutton. Upon penetration, the tip moves in a proximal direction for a small "float distance" until it is restrained by the mechanism. After penetration has been fully completed, the force on the tip decreases and the tip will move distally a short distance, after which a main spring will operate to retract the obturator and thereby the tip. At the end of the retraction, the pushbutton will be unlocked and returned to its normal position extended from the rear of the grip, thus giving a visual indication that the trocar is ready for another cycle.

Another advantage is that the instant device uses a series of linkages, tracks and springs which are designed to isolate the various motions and forces for purposes of "tuning." For example, a large main spring is used for firing, while a smaller secondary spring is used to control the "float distance." In this manner, the springs can be independently selected for their particular function. This also prevents the trocar from "jumping" in the surgeon's hand during point retraction. Still another advantage is the ability to recock the mechanism if it has been fired prematurely, and to do so with ease and with one hand. The palm cock pushbutton facilitates this. Such premature firing can occur due to surgeon technique of hesitation or withdrawal.

The features and advantages described in the specification are not all inclusive, and particularly, many additional features and advantages will be apparent to one of ordinary skill in the art in view of the drawings, specification and claims hereof. Moreover, it should be noted that the language used in the specification has been principally selected for readability and instructional purposes, and may not have been selected to delineate or circumscribe the inventive subject matter, resort to the claims being necessary to determine such inventive subject matter.

BRIEF DESCRIPTION OF THE DRAWINGS

FIG. 5 is a top plan cross-sectional view of the inventive trocar in its initial, protected position within the trocar tube.

FIG. 6 is a similar view showing the sharp pointed tip of the obturator extended from the trocar tube after depressing the palm cock pushbutton.

FIG. 7 is a view of the same with the tip having traveled a small distance back into the trocar tube upon being thrust through a body wall.

FIG. 8 is a view of the same with the tip being fully retracted and the palm cock pushbutton returned to its original position.

FIG. 9 is a partial, inverted cross-sectional view taken along lines 9—9 in FIG. 1.

FIG. 10 is a top plan cross-sectional view of an alternate embodiment wherein the obturator is of reduced diameter to minimize frictional drag from contact with the flapper valve.

DETAILED DESCRIPTION OF THE PREFERRED EMBODIMENT

FIGS. 1 through 15 of the drawings depict various preferred embodiments of the present invention for purposes of illustration only. One skilled in the art will readily recognize from the following discussion that alternative embodiments of the structures and methods illustrated herein may be employed without departing from the principles of the invention described herein. Generally, FIGS. 1 through 10 depict one embodiment of the present invention and FIGS. 11 through 15 depict another embodiment.

Figure 1:
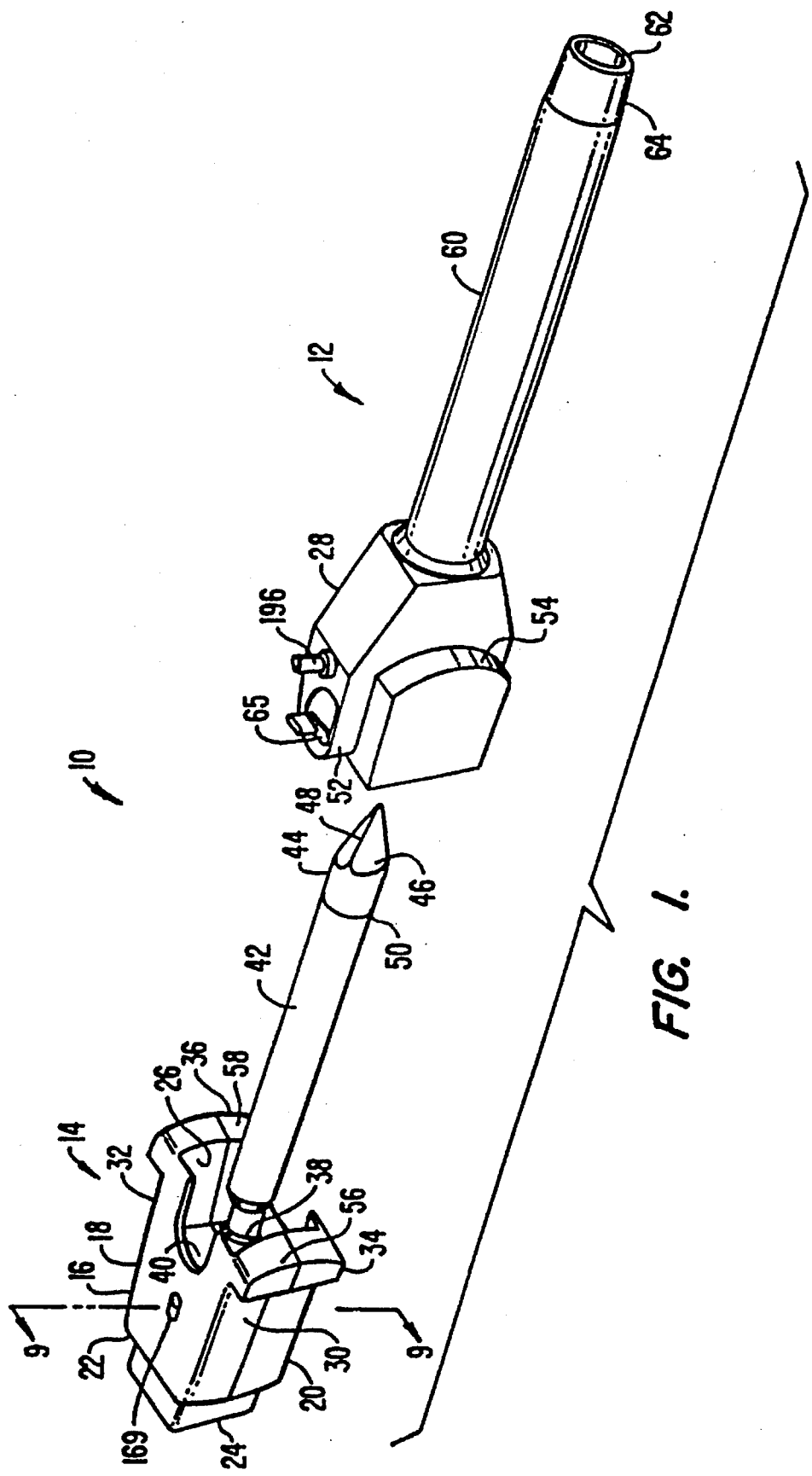
FIG. 1 is an exploded top quarter isometric view of the inventive trocar showing its two subassemblies.

As shown in FIG. 1, the trocar assembly 10 consists of two basic subassemblies: a trocar tube subassembly 12 and a co-axial trocar body subassembly 14. The two subassemblies are designed to be separable from each other as shown. Trocar body subassembly 14 includes a head or grip 16 made up of top and bottom halves-18, 20, respectively. These top and bottom halves may be made of plastic material such as ABS plastic. The grip 16 is generally rectangular with a rounded rear end wall 22 adapted to fit the palm of the hand of the surgeon. Axially projecting from the rear end wall is a movable pushbutton 24 which will be more fully described hereafter. Located in the distal end of the grip is a slot 26 which is dimensioned to closely receive a correspondingly shaped trocar tube body 28.

The slot 26 defines a pair of spaced parallel arms 30, 32 having wings 34, 36 extending laterally therefrom. Projecting from an aperture 38 in front wall 40 within slot 26 is an elongated obturator 42, which may be conveniently be made of plastic, aluminum or other metal material. A sharp piercing tip or point 44, which may conveniently be made of aluminum or stainless steel material, is fixedly mounted on the distal end thereof. The piercing tip is formed by the intersection of three angled surfaces, two of which are shown at 46, 48. The obturator 42 has a tapered surface which narrows from its distal end 50 to its proximal end to facilitate movement through body tissue. It also has a reduced diameter portion 49 where it enters aperture 38 thereby to facilitate movement through valve body seal 51, as seen in FIG. 5.

Returning to FIG. 1, the trocar tube body 28 may be made of plastic material such as ABS plastic. Rounded rear portion 52 of trocar tube body 28 fits within a correspondingly-shaped portion of grip 16. When in this fully engaged position, rounded front walls of the trocar tube body, one of which is shown at 54, will be in register with correspondingly-shaped front walls 56, 58 of grip 16. In this manner, the surgeon can conveniently grip the trocar by placing a finger on each front wall 56, 58 while holding the rounded rear wall 22 and pushbutton 24 in the palm of the hand.

Projecting from the trocar tube body 28 in a distal direction is a tubular trocar tube or cannula 60, which may also be of ABS plastic. The tube 60 has an angled opening 62 and a tapered end portion 64 to facilitate travel through the body wall. A valve lever 65 movable in a recess 66 on the top of the trocar tube body 28 permits opening a flapper valve (not shown), as will be described hereafter.

Figure 2:
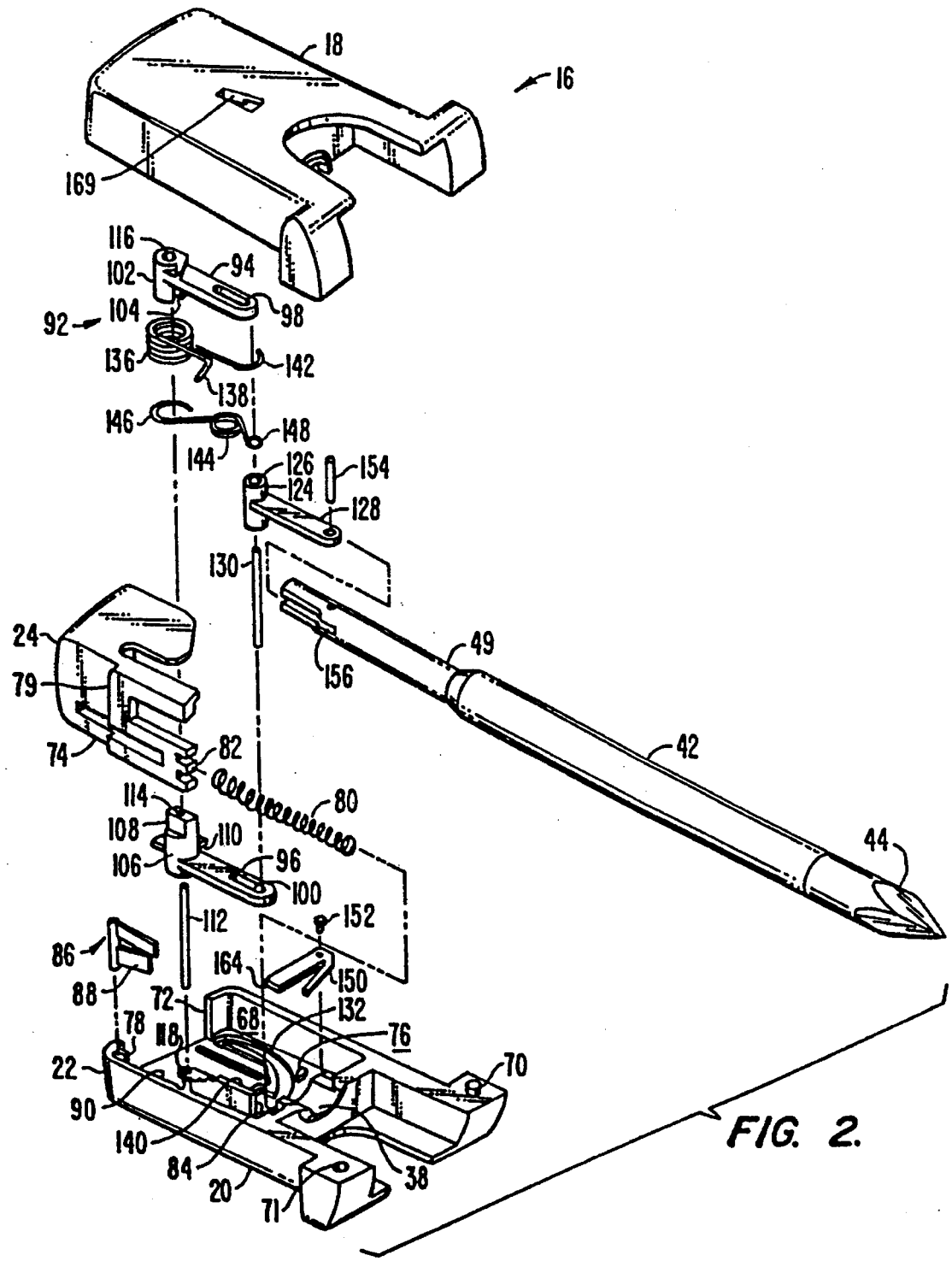
FIG. 2 is an exploded top quarter isometric view of one of the subassemblies of FIG. 1, namely, the trocar body subassembly.

Turning to FIG. 2, the trocar body subassembly will now be described. As seen in this figure, top half 18 and bottom half 20 of grip 16 define a hollow chamber 68 therebetween. The top and bottom halves may be conveniently held together by fasteners, such as pins 70, press fit into accommodating holes 71 in the top and bottom halves. Pushbutton 24 projects through generally square aperture 72 in the rear end wall 22 of grip 16. Pushbutton 24 includes a rectangular rail 74 on its bottom that slides in a correspondingly-shaped track (not shown) in wall 76 of bottom half 20. Travel in the proximal direction is limited by a stop 78 molded into the half 20. A vertical ridge 79 molded in the lateral wall of the pushbutton 24 is biased against the stop 78 by means of a pushbutton coil spring 80. This coil spring is held in place between a projection 82 on pushbutton 66 and a projection 84 on the interior of the bottom half 20.

Figure 3:
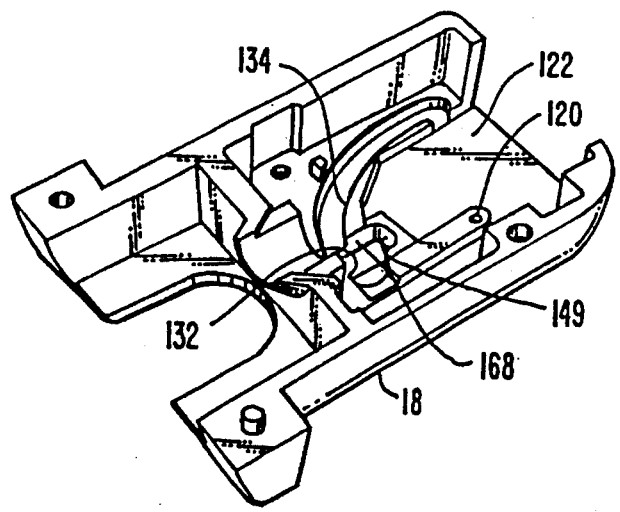
FIG. 3 is a bottom quarter isometric view of the top housing of the trocar body shown in FIG. 2.

A bifurcated locking member 86 includes a bottom leaf 88 which is normally located in the path of ridge 79 so as to lock the pushbutton in its fully depressed position. Locking member 86 fits within and is retained by elongated groove 90 in a side wall of chamber 68. Located within the chamber 68 is a rotator assembly 92. The rotator assembly consists of upper and lower link members 94, 96. These link members have elongated slots 98, 100 in their proximal ends. Upper link member 94 has extending therefrom at its proximal end an integral cylindrical shaft 102 with a vertical groove 104 therein. Similarly, lower link member 96 has an upwardly directed cylindrical shaft 106 with a tongue 108 dimensioned to be closely fitted within groove 104. An integral cam 110 on shaft 106 serves to depress leaf 88 at the end of a cycle to permit pushbutton 24 to return to its normal position extended from grip 16. Pin 112 passes through holes 114 and 116 in upper and lower link members 94, 96 respectively. The lower end of pin 112 is restrained in hole 118 in the interior wall 76 of lower half 20. Similarly, and as best seen in FIG. 3, a hole 120 is provided in the inner wall 122 of upper half 18 to accommodate the upper end of pin 112.

Returning to FIG. 2, a cylindrical shaft 124 having a bore 126 therethrough is integrally connected to a middle link member 128. A pin 130 passes through this bore and the ends of pin 130 pass through slots 98, 100 and are movable therein. The lower end of pin 130 travels in an arcuate groove 132 molded within wall 76 of lower half 20. Similarly, and turning to FIG. 3 again, the upper end of pin 130 travels in arcuate groove 134 in upper half 18. Returning to FIG. 2, main torsion spring 136 is wrapped about shaft 106. One free end 138 of the spring is bent at right angles and contacts interior side wall 140. The other end 142 is curved and wrapped around shaft 124. Secondary torsion spring 144 has its free ends 146, 148 wrapped around shafts 106 and 124 respectively. A latch 150 is fixed to inner wall 76 by means of screw 152.

The rotator assembly 92 is connected to obturator 42 by means of a pin 154 which secures middle link member 128 within slot 156 in the proximal reduced diameter portion 49 of obturator 42. Pivotal movement of the rotator assembly 92 about pin 112 thereby is transmitted to obturator 42 through links 94, 96, shaft 124 and link 128, so as to reciprocate the reduced diameter portion 49 of obturator 42 in aperture 38.

Referring to FIG. 5, the trocar assembly 10 is shown in its initial position for storage, transportation, and pre-stick clinical handling. In this position and condition, the trocar tip 44 resides within and spaced from the open end 62 of trocar tube 60. Pushbutton 24, the top portion of which has been cut away for purposes of clarity, extends rearwardly through aperture 72 in grip 16 in a position to be actuated by the palm of the surgeon's hand when the first and second fingers are in position on front walls 56, 58. In order to move the tip 44 to its fully extended or "cocked" position (FIG. 6), the pushbutton 24 is depressed by the palm in a distal direction. The distal edge 158 of pawl 160 which is fastened to the bottom wall of pushbutton 24 is in a position to contact and move link 96 of rotator assembly 92. Rotator assembly 92 pivots around pin 112 so as to move middle link 128, obturator 42 and tip 44. The pawl 160 rides over a ridge 162 in shaft 106, as best seen in FIG. 9, so that it no longer rests on link 96 when the pushbutton 24 is depressed, enabling the tip 44 to fire even when the pushbutton is depressed. This is because the linkage is free to move into the pushbutton.

As shown in FIG. 6, bottom leaf 88 in locking member 86 springs out to catch ridge 79 and thereby prevent rearward distal movement of the pushbutton 24. The pushbutton is held in this depressed position until a cam 110 integral with link 96 and shaft 106 pushes bottom leaf 88 laterally away from ridge 79. This does not occur until the tip 44 is almost fully retracted. When this happens, pushbutton spring 80 causes the pushbutton 24 to return to its initial extended position shown in FIG. 5, and the trocar is again ready for use.

Continuing with FIG. 6, the trocar obturator 42 is shown fully advanced with tip 44 penetrating a body wall shown in dotted lines. In its fully extended position shown, the tip 44 is located a distance d1 of about 0.1875 inches from open end 62 of trocar tube 60. In this position, pin 130 is at the distal end of slot 98 and on the side edge 164 of latch 150. In this position, the force due to penetration, which may be about 4–10 pounds, is distributed to trocar body subassembly 14 by means of pin 130 contacting the body. For example, force is distributed to body 14 by means of the pin seating in the apex 149 of grove 134. (See: FIG. 3.) Latch 150 prevents pin 130 from entering arcuate groove 132.

As shown in FIG. 7, tip 44 moves in a proximal direction so that the distance between the tip and open end 62 falls to a distance d2 of about zero. Thus the tip will have moved proximally a "float distance" of about 0.1875 inches upon penetration of the body wall. At the same time pin 130 moves to the proximal end of slot 98 against the biasing force of secondary spring 144, which may be about 2 pounds. Pin 130 also moves off the edge 164 of latch 150. As the pin 130 continues to travel along slot 98, the secondary spring 144 is compressed until the pin has traveled the full 0.1875 inches along the slot. If there is a small change in force at the body wall, the pin 130 will move in the slot and such minor movement will be accommodated by the "float distance" of the slot without premature triggering of the device. The tip 44 will not begin to retract until the force from the body wall is reduced to zero and the pin 130 has traveled back towards the distal end of the slot 98 a portion of the float distance.

When pin 130 travels back, it will no longer contact edge 164 of latch 150. Rather, it will contact generally perpendicular edge 166 of latch 150, due to the fact that main spring 136 will have moved link 96 laterally. In this position, pin 130 will be restrained from moving laterally by a wall 168. (See: FIG. 3). Secondary spring 144 will then move pin 130 against and compress latch 150 so that pin 130 moves free of the restraining action of wall 168 and into arcuate groove 132. Main spring 136, which may be about 6 pounds of force, will then cause pin 130 to follow the arcuate path of groove 132, as shown in FIG. 8, until it reaches its most proximal position shown in FIG. 5. In doing so, it retracts tip 44 through the linkage mechanism thus described. By having secondary spring 144 at about 2 pounds of force while main spring 136 is about 6 pounds of force, this will allow the tip 44 to be set easily while the stiffer main spring will cause rapid firing. It may be noted that the mechanism does not immediately retract upon reduction of force on the tip. Rather, there must first be a movement of the tip in the distal direction a short distance before this occurs.

Again, as bottom link 96 reaches the end of its rotation in the counter-clockwise direction, a cam 110 will depress leaf 88 of locking member 86 so as to release pushbutton 24. Pushbutton 24 will then be moved rearwardly in the proximal direction by the force provided by spring 80 to the fully extended position shown in FIG. 5, so that the trocar body subassembly 14 is ready for another cycle. The return of the pushbutton to the extended position also gives visual indication of this condition. Another visual indicator is provided by a small window 169 in top half 18 of grip 16, as best seen in FIG. 2. When tip 44 is fully advanced, the end of pin 130, which may be painted a highly visible color, appears in window 169. When the tip has retracted, pin 130 will no longer be visible in the window.

With the pushbutton mechanism thus described, a mechanical advantage will be produced of the order of 2:1. That is, compression of pushbutton 24 its full length of travel of about one-half inch will be translated by the mechanism into about 1 inch travel of the tip 44.

Figure 4:
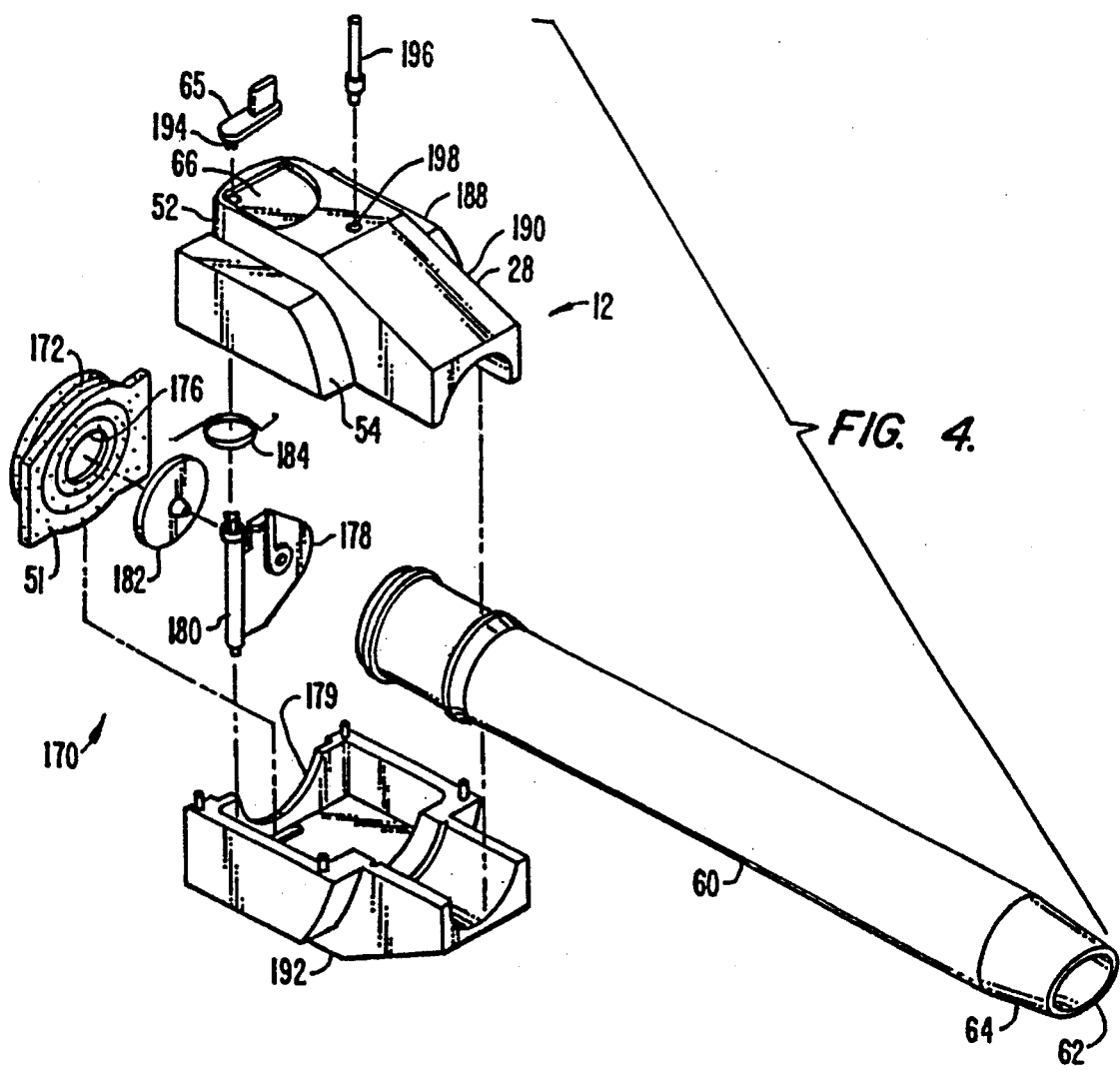
FIG. 4 is an exploded top quarter isometric view of the other of the subassemblies of FIG. 1, namely, the trocar tube subassembly.

After the trocar tube subassembly 12 is in place providing communication within the patient, the trocar body subassembly 14 may be manually removed. As best seen in FIG. 4, within head or grip 16 is a flap valve mechanism generally at 170. The flap valve mechanism includes generally circular seal 51 of deformable material such as rubber, having a circular opening 176 therethrough for admitting the obturator. Seal 51 is mounted within an aperture 178 in the proximal end of housing 16 by means of an annular groove 172. Aperture 176 serves as a port for the entry of instruments and the like during surgery.

The flap valve mechanism further includes a generally

U-shaped valve 179 mounted along a vertical edge thereof to an integral shaft 180. The shaft 180 is pivotally mounted at opposite ends thereof in holes (not shown) in the grip 16. A circular pad 182, which may be made of plastic material such as Tygon plastic, is fixed to valve 179 by suitable means. A coil spring 184, which is positioned over shaft 180, biases flap valve 178 to normally close off aperture 176 when the obturator 42 is removed. In this manner, unwanted foreign matter such as bacteria or the like is prevented from entering aperture 176, and thereby entering the patient, through tube 60.

Trocar tube subassembly 12 includes a hollow body or housing 188, having a top portion 190 and a bottom portion 192. A lever 65 may be rotated within fan-shaped recess 66 molded in top portion 190. Lever 65 has a shaft 194 depending therefrom that may be fixed to the upper end of shaft 180 by suitable means. In this manner, rotation of lever 65 will cause valve 178 to be opened against the biasing force of spring 184.

In addition, the trocar tube subassembly also includes a conventional one-way check valve which is fixed within an aperture 198 in top portion 190. Valve 196 may be connected to a source of insufflation gas, which may be admitted to the patient cavity through housing 188 and trocar tube 60. Alternatively, a stopcock valve may be used.

In an alternate embodiment shown in FIG. 10, the obturator shank 49 at its distal end is shown to be of reduced diameter from that shown in the previous figures. This reduces the frictional drag on the obturator induced by main seal opening 176 during its movement, which is important to ensure smooth operation of the device. The reduced diameter also increases the angle "A" at which flap valve 178 contacts the obturator shank 49, and thus reduces the spring force (since the spring is less compressed in this position), thereby reducing the friction which is a function of the force imposed by the valve.

Figure 11:
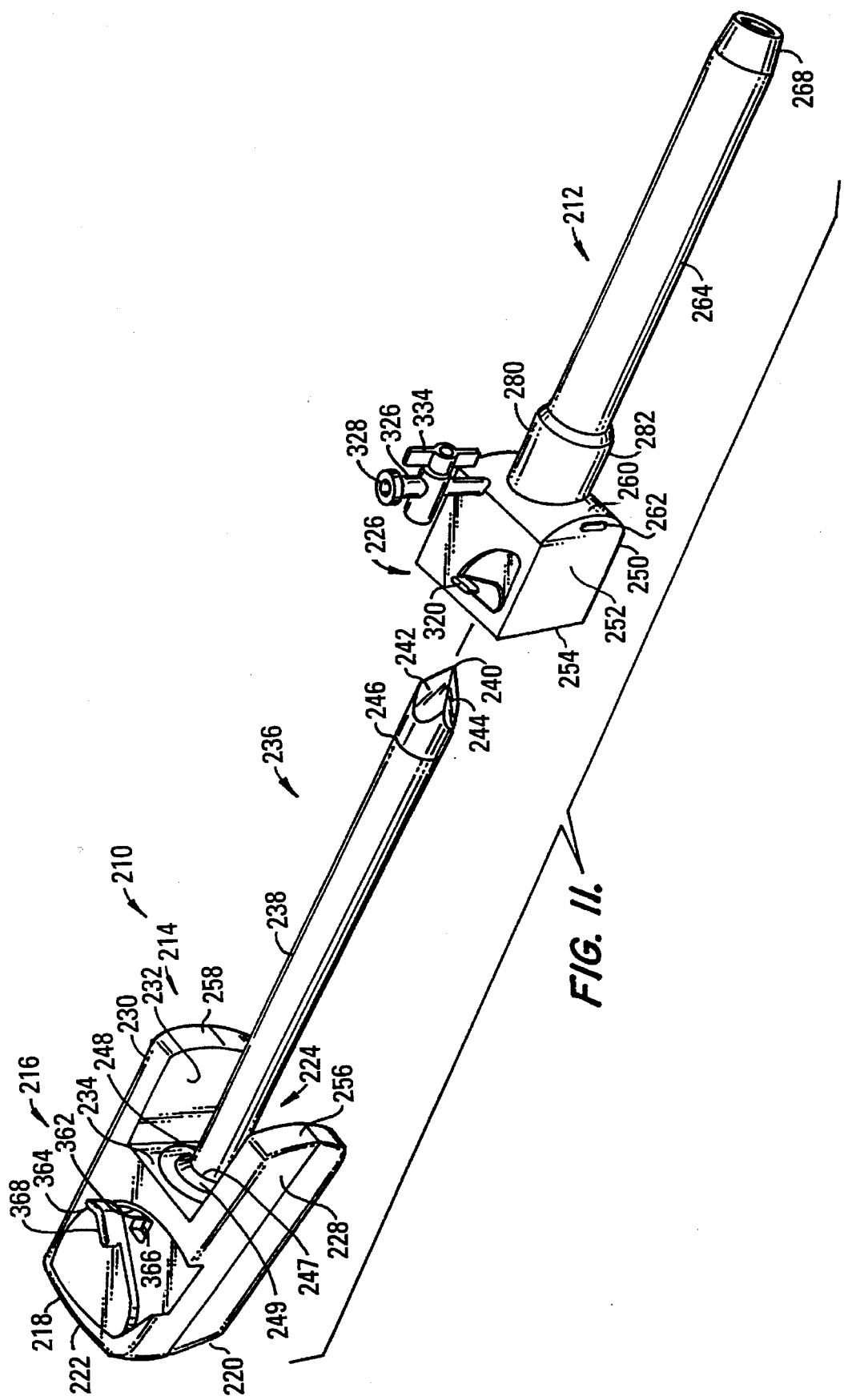
FIG. 11 is an exploded top quarter isometric view of the inventive trocar showing its two subassemblies.

Turning now to another embodiment, as shown in FIG. 11, a trocar assembly 210 consists of two subassemblies: a trocar tube subassembly 212 and a trocar body subassembly 214. The two subassemblies are designed to be separable from each other. Trocar body subassembly 214 includes a head or grip 216 made up of top and bottom halves 218 and 220, respectively. These top and bottom halves may be made of plastic material such as ABS plastic. The head 216 is generally rectangular with a rounded rear wall 222 adapted to fit the palm of the hand of the surgeon. The front of the head has a rectangular slot 224 therein which is dimensioned to closely receive correspondingly shaped trocar tube body 226, as best seen in FIGS. 12A–12D.

Returning to FIG. 11, the slot 224 in head 216 defines a pair of spaced, parallel arms 228, 230 having a pair of opposing side walls, one of which is shown at 232. Projecting between the arms centrally and disposed from front wall 234 is a stylet 236. Styler 236 is comprised of an elongated obturator 238, which may conveniently be made of aluminum or other material. Styler 236 has a sharp piercing tip or point 240 which may conveniently be made of aluminum or stainless steel material fixedly mounted on the distal end thereof. The piercing tip is formed by the intersection of three angled surfaces, two of which are shown at 242, 244. The obturator has a tapered surface which narrows from its distal end 246 to its proximal end 248, where it enters aperture 247 in frustoconical projection 249 on the front wall 234 in order to reduce friction and thereby facilitate its movement through body tissue.

Trocar tube subassembly 212 has a body 250, which may be made of plastic material such as ABS plastic, which is dimensioned to closely fit within slot 224. In this position the side walls of the body 250, one of which is shown at 252, will closely contact the accommodating side walls of the head 216. At the same time, a rear wall 254 of the trocar tube body 250 will closely contact front wall 234 of head 216. When in this position, the rounded front walls 256, 258 of head 216 will be in register with a correspondingly shaped rounded front wall 260 of trocar tube body 250. In this manner, the surgeon can conveniently grip the head 216 by placing a finger on each front wall 256, 258, while holding the rounded rear wall 222 in the palm of the hand.

In order to hold the two subassemblies 212, 214 together, projections (one of which is shown at 262), are molded into the side walls of trocar tube subassembly 212. Projecting from the front wall 260 of the tube body 226 is an elongated trocar tube or cannula 264, which may be made of plastic material such as ABS plastic, having a distal end 266 which has a tapered frustoconical surface 268. As best seen in FIG. 14B, the principal elements of the trocar tube subassembly 212 are: the body 226, which is made up of generally symmetrical upper and lower halves 270, 272 which are held together by a plurality of pin projections 274 in lower half 272, which mate with corresponding bores (not shown) in top half 270; and the trocar tube 264 having a circumferential ring 276 formed thereon adjacent its proximal end which fits within annular groove 278 in mating semicircular projections 280, 282. Another ring 284, which is spaced from ring 276 and formed on said trocar tube 264 intermediate ring 276 and the distal end 266 of tube 264, functions to seal off the semicircular openings 286, 288 in projections 280, 282, respectively. While pin projections have been shown, it is to be understood that other fastening means such as screws or adhesive could alternatively be used.

Within chamber 290 formed by the body halves 270, 272 is a flap valve mechanism 292. The flap valve mechanism includes: a generally circular grommet-like seal 294 of deformable material such as rubber, having a groove 296 therearound for mounting in a pair of semicircular holes, one of which is shown at 298 in lower half 272 and having central opening 300 therethrough; a generally U-shaped valve 302 mounted along one edge thereof to a vertically oriented shaft 304, the shaft being pivotally mounted at its upper and lower ends 306, 308 in holes in the tube body, one of which is shown at 310; a circular pad 312, which may be made of a plastic material such as Tygon plastic, fixed to the valve 302 by means of an integral projection 314 which engages bore 316 through the center of valve 302; and a spring 318 which fits over shaft 304. The spring 318 biases valve 302 and thereby pad 312 to normally close off opening 300 when the styler (not shown) is removed. The function of the flap valve mechanism is to act as a closure when the trocar tube subassembly is removed from the trocar body subassembly.

Parenthetically, grommet-like seal 294 is adapted to seal with the frustoconical projection 249 on the front wall 234 of head 216 (see FIG. 11). Also a part of the flap valve mechanism is an actuating lever 320 which is mounted on the upper end 306 of the shaft exteriorly of the body 272. The exterior top surface 322 of the body has a fan-shaped recess 324 molded therein within which the lever 320 is free to move. The lever 320 allows the valve to be manually opened for admission of surgical instruments. Completing the tube assembly is a valve or stopcock 326 having a valve inlet 328 and a valve outlet 330. A tapered frustoconical portion 331 of the valve 330 is inserted into a bore 332 in top half 270. The valve is actuated by means of rotating a valve handle 334 so as to selectively open or close off communication between inlet 328 and outlet 330, thereby facilitating the admission of insufflating gas to the body cavity.

Figure 13:
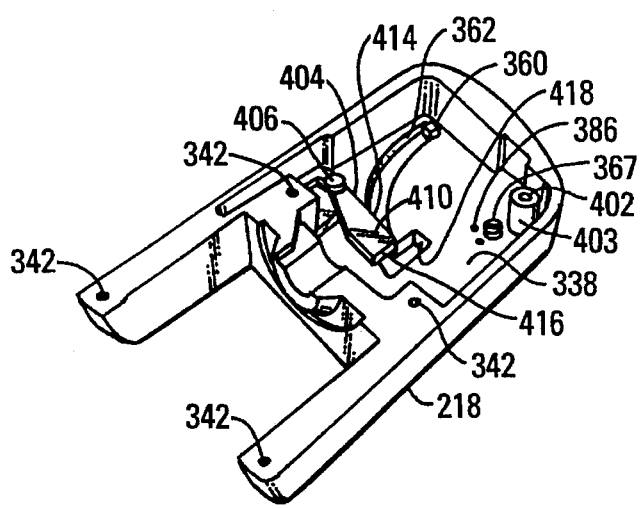
FIG. 13 a top quarter isometric view of the interior of the top half of the trocar head or grip showing details thereof.
Figure 14A:
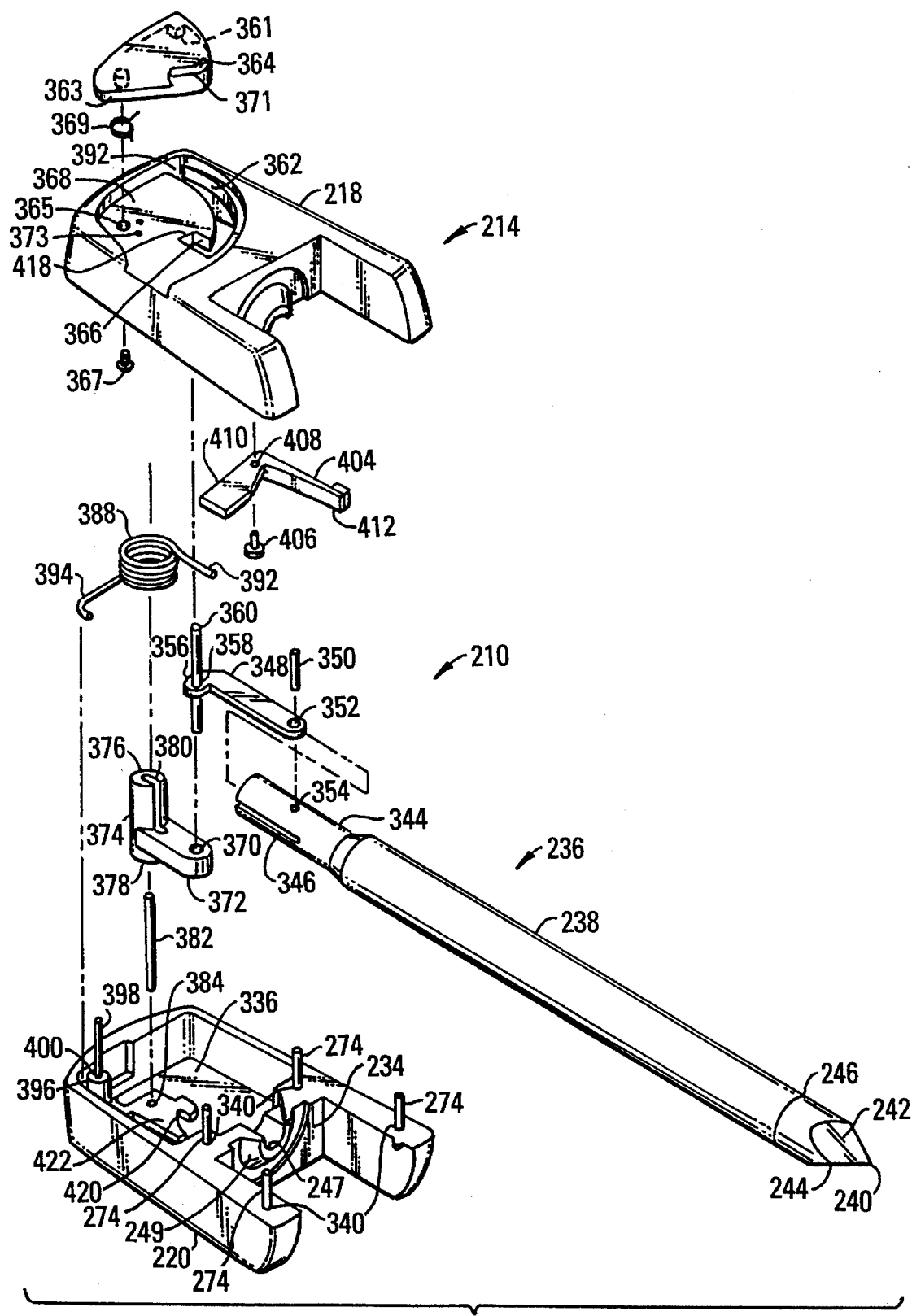
FIG. 14A is an exploded top quarter isometric view of the trocar body subassembly.
Figure 14B:
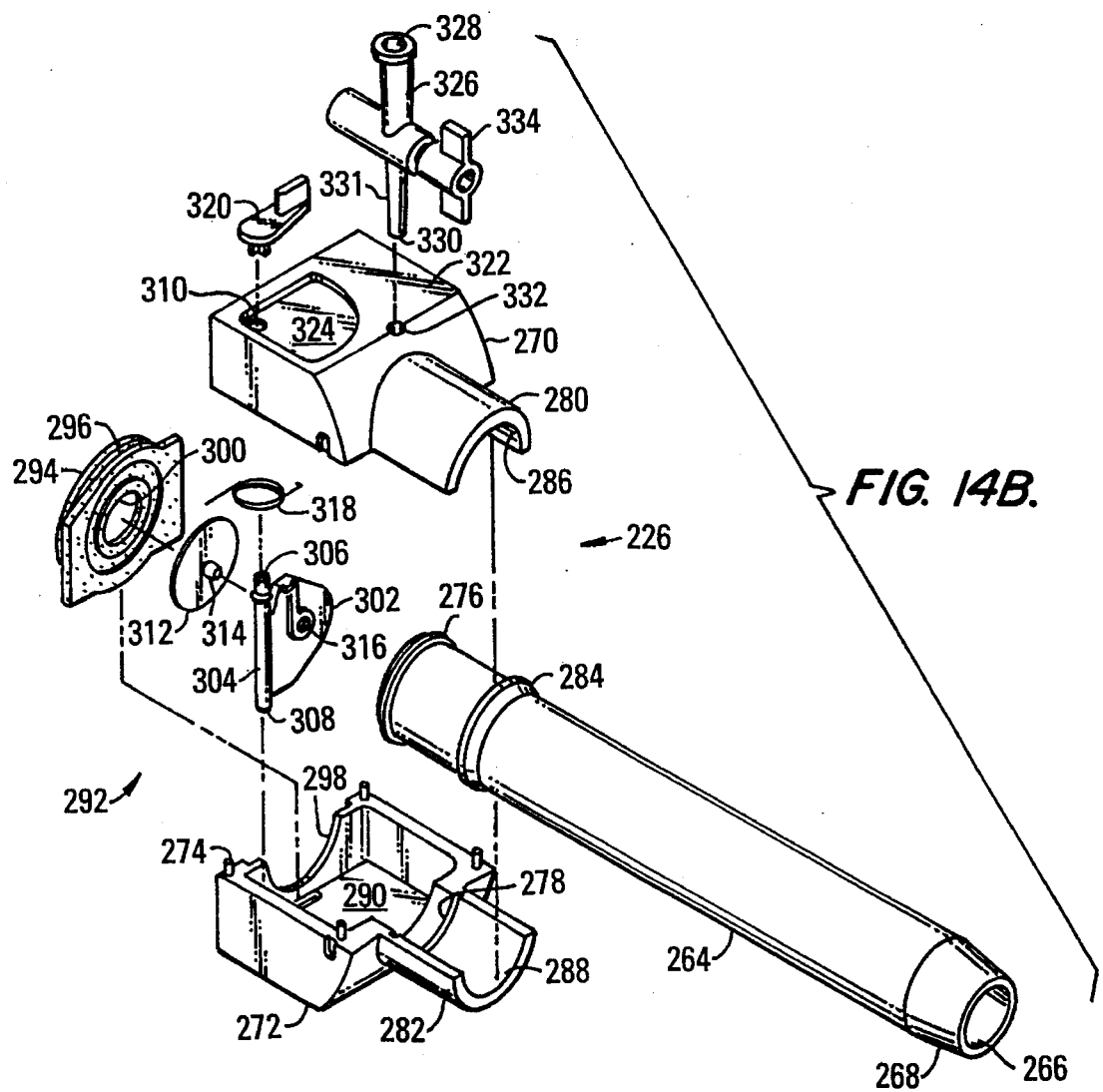
FIG. 14B is an exploded top quarter isometric view of the trocar tube subassembly.

Turning now to FIG. 14A, the top and bottom halves 218, 220 are exploded to show details of the interior mechanism of trocar body subassembly 14. As may be seen, a cavity 336 is formed in the bottom half 220. As best seen in FIG. 13, a mating cavity 338 is formed in top half 218. Returning to FIG. 14A, the top and bottom halves are joined together by means of a plurality of metal pins 274 or other convenient fastening means. As may be seen, these pins are press fit into accommodating bores 340 in bottom half 220. As may be seen in FIG. 13, the opposite ends of these pins are adapted to be press fitted into a plurality of bores 342 in top half 218.

Again returning to FIG. 14A, styler 236 has a reduced diameter shank portion 344 which is dimensioned to be axially slidable in an aperture 247 in front wall 234 and projection 249. An elongated horizontally disposed slot 246 is formed in the proximal end of shank 344. This slot is adapted to receive lever arm 348. Lever arm 348 is pivotally connected at its distal end to shank 344 by means of a pivot pin 350 which passes through bore 352 in the distal end of lever arm 348 and is press fit into bore 354 which is drilled through shank 344. The proximal end of lever arm 348 has a lateral projection 356 at a right angle to the direction of lever arm 348 and a bore 358 therethrough. An elongated actuator pin 360 is fixedly mounted within said bore intermediate its ends by welding or other convenient means.

The upper end portion of actuator pin 360 extends into an arcuate slot 362 in top half 218 and has an actuating lever 364 mounted thereon. A projection 361 depending from the underside of actuating lever 364 travels in groove 362 and is adapted to contact and move pin 360 when the lever is rotated about pivot 363 within aperture 365 in top half 218. Lever 364 is retained within aperture 365 by means of a retainer screw 367 threadedly engaged within an axial bore in pivot 363. The slot 362 is cut to the rear so as to form an axially directed wall 366 for a purpose to be described hereinafter. Material is cut away so as to form an indentation 368 in top half 218. An upward projection 371 facilitates manipulation of lever 364. Shaft 360 is of such a length as to permit a free end thereof to travel within slot 362. A spring 369 around and fixed at one end to pivot 363 and at the other end to a hole 373 in top half 218 biases lever 364 to the position shown in FIG. 11. In the fully retracted position, pin 360 is permitted to reach a position near bottom wall 392 within slot 362 (see FIG. 14A).

The lower portion of actuator pin 360 extends through and is freely pivotable within a bore 370 in lever arm 372. Lever arm 372 is in turn fixed at its opposite end to cylindrical member 374 intermediate its upper and lower ends 376, 378. A slot 380 extends through the length of member 374. This slot is in line with the direction of lever arm 372. A pivot pin 382 passes through slot 380. The lower end of pivot pin 382 is fixed within bore 384 in the bottom of cavity 336. The upper end is adapted to be fixed within bore 386 in cavity 338 in upper half as seen in FIG. 13. Returning to FIG. 14A, a coil spring 388 has a body portion adapted to encompass member 374. One end 392 of coil spring 388 is adapted to bear against and bias actuator pin 360 against wall 366 and towards the bottom 392 of arcuate slot 362. The other end 394 of coil spring 388 has a curved end and contacts a cylindrical projection 396 that extends from the bottom of cavity 336. A pin 398 is press fit within a bore 400 within projection 396. This pin is adapted to fit within a bore 402 in a corresponding cylindrical projection 403 in cavity 338 as seen in FIG. 13. As seen in this figure and in FIG. 14A, an L-shaped latch 404 is mounted within cavity 338 by means of a screw 406 which passes through a bore 408 at the juncture of the two arms 410, 412 of the latch. The latch 404 may conveniently be injection molded of plastic material.

Figure 15:
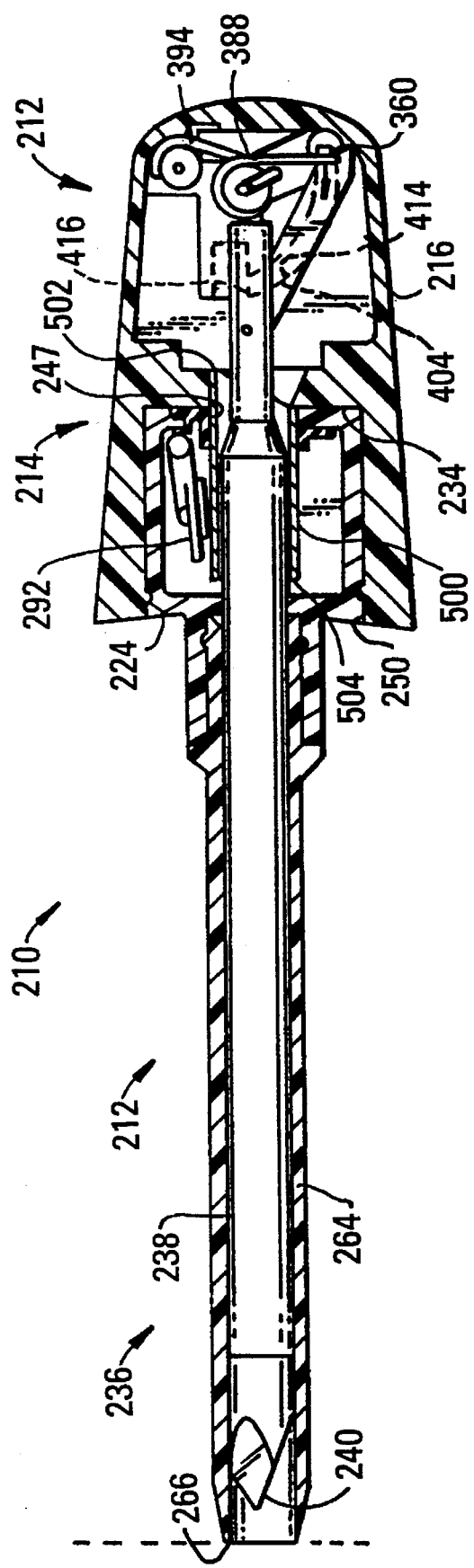
FIG. 15 is a top plan cross-sectional view of an alternate embodiment having structure for reducing drag on the stylet.

Turning to FIG. 15, there is shown an alternate embodiment of the invention which includes a mechanism for reducing frictional drag on the obturator 238 and thereby on the stylet 236. The drag reduction mechanism comprises a hollow tube 500 which may conveniently be of stainless steel material. The tube is fixedly mounted in an aperture 247 in frustoconical projection 249 on the front wall 234 of head 216 as by press fitting its proximal end 502 therein. The tube is of a length from its proximal end 502 to its distal end 504 so as to hold flap valve mechanism 292 out of contact with the obturator 238 when the two subassemblies 212, 214 are fully engaged as shown. The inner diameter of tube 500 is slightly larger than the outer diameter of obturator 238 so that no frictional drag is imparted to the obturator by the flap valve mechanism 292 when the obturator moves axially incident to operation of the trocar. Tube 500 will eliminate any frictional impedance that would tend to slow the action of spring 388 upon retraction of obturator 238.

The operation of the trocar will now be discussed as follows. Prior to use, the trocar tube assembly 210 will be in the assembled form shown in FIG. 12A. In this form, trocar tube subassembly 212 will have its body 250 nestled within slot 224. Obturator 238 of styler 236 will be positioned as shown within trocar tube 264. In this initial position or state, tip 240 is recessed within the tube and spaced from the distal end 266. In this manner, the tip is prevented from causing injury during transport. In order to place the trocar in operational condition or form, actuator pin 360 is manually advanced in the arrow direction by moving lever 364 by projection 371 so that projection 361 moves pin 360 as shown in FIG. 14A until it reaches the end of its travel in slot 362. Near the end of its travel, pin 360 will contact rearward-facing transverse edge 414 of latch 404, which projects into slot 362 (see FIG. 13).

Figure 12A:
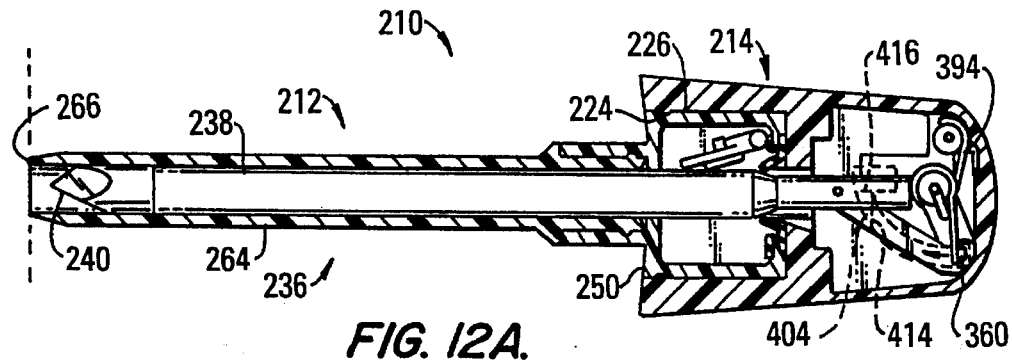
FIG. 12A is a top plan cross-sectional view of the inventive trocar in its initial protected position.
Figure 12B:
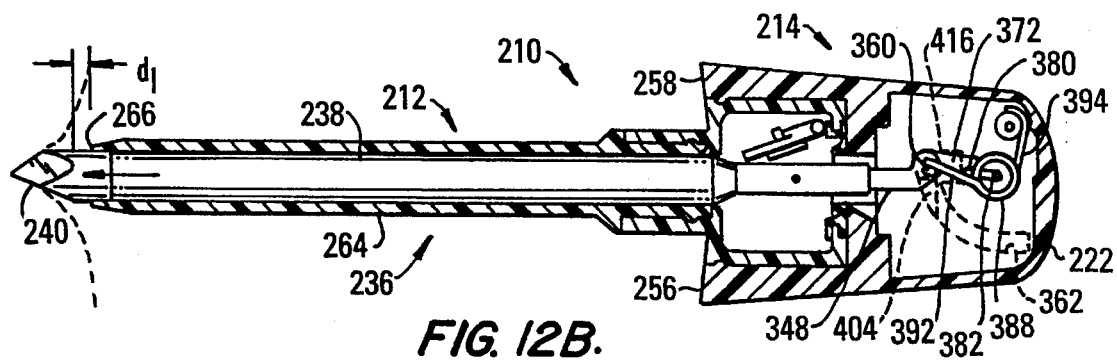
FIG. 12B is a similar view showing the trocar advanced from its protective tube.

Continued movement of pin 360 will move the latch to the left or distal direction as shown in FIG. 12A until it passes axial edge 416. At this moment, the biasing force of latch 404 will return it to its initial position and pin 360 will be held against axial edge 416, as best seen in FIG. 12B. It will be held in this cocked position by the biasing force of coil spring 388 applied through spring end 392.

In this cocked position, the tip 240 projects a distance $D_1$ from distal end 266 of tube 264. Arm 348 and lever arm 372 will be axially aligned with stylet 236. As shown in this figure, the trocar is manually advanced against the body tissue shown in dotted lines defining the wall of a body cavity. The trocar is inserted through the tissue defining the wall of the body cavity. In practice, this insertion is made through a small incision in the skin that is created for this purpose.

Figure 12C:
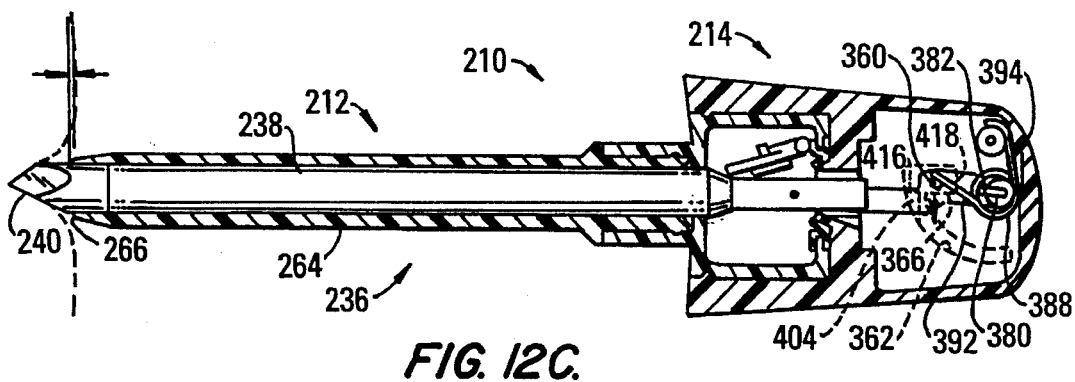
FIG. 12C is a further view of the same showing the styler locked into position just prior to piercing a body wall.

The trocar is gripped firmly in the hand with the rounded rear wall 222 of the head 216 against the palm and the index and middle fingers extending around the front walls 256, 258 of the trocar body subassembly 214 on either side of tube 264. The reactant force of the tissue will cause a slight "float distance" movement of the stylet 236, arm 348 and lever arm 372 in the proximal direction until the position seen in FIG. 12C is achieved. In this position, the distance between the tip and the open end 266 falls to a distance $D_2$ of about zero. This small amount of excess movement called the "float distance" is made possible by slot 380 in cylindrical member 374. Parenthetically, the "float distance" may be in the range of 0.050 to 0.1875 inches, with 0.125 inches as an optimum.

The movement of pivot pin 382 in slot 380 is designed to be greater than the movement required to release latch 404. The slight additional movement of pin 382 within slot 380 allows for slight changes in surgeon advancement rate or variations in tissue density or resistance to not trigger latch 404 and retract the point 240 prior to penetrating the body cavity.

This movement of pin 382 in slot 380 of cylindrical member 374 will now be described in further detail. In this position, pivot pin 382 is located at the distal end of slot 380 and end 394 of coil spring 388 is rotated so as to produce a biasing force in the distal direction. At the same time, actuator pin 360 moves in the proximal direction until it is free of contacting axial edge 416. The lateral biasing force of end 392 of coil spring 388 causes actuator pin 360 to move laterally until it seats against wall 366 and the apex 418 of slot 362. In this position, the final force generated by tip 240 passing through the tissue is resisted by a positive stop formed in top half 218 in the area of contact between pin 369 and apex 418 where wall 366 intersects slot 362. The balance of the force thus generated will be transmitted to bottom half 220 by means of actuator pin 360 contacting apex 420 formed in a raised portion 422 within cavity 336, as best seen in FIG. 14A.

Figure 12D:
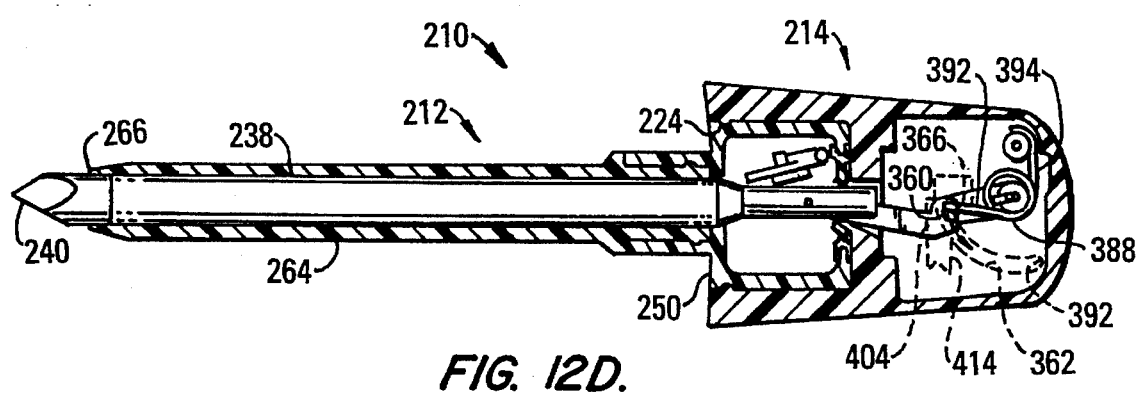
FIG. 12D is a still further view of the same showing the stylet beginning to retract after passing through the body wall.

After the tip passes through the tissue and enters the body cavity, the force on the tip will decrease and in fact cease. As soon as this resistant force is less than a threshold value supplied by the biasing force of end 394 of coil spring 388, actuator pin 360 will move in a distal direction under the influence of such biasing force. As seen in FIG. 12D, actuator pin 360 will move distally against edge 414, compressing and moving latch 404 in a distal direction, since the force generated by end 394 of coil spring 388 is greater than that generated by latch 404. As soon as actuator spring 360 moves distally enough to clear contact with wall 366, it will enter slot 362 and move in the arrow direction under the biasing influence of end 392 and spring 388. Actuator pin 360 will move along the arcuate path defined by slot 362 until it is stopped by projection 361 (see FIG. 14A), against which it bears, reaching the slot bottom 392. It will thus have automatically returned to the position shown in FIG. 12A with the tip 240 fully retracted into tube 264. Of course, unlike the FIG. 12A situation, tube 264 will be within the body cavity. In this manner, viscera and other internal tissues are protected from contact with the piercing tip and potential damage that it might cause. At the same time, the surgeon has a visual indication, by the lever 364 (see FIG. 11) being fully retracted, that the tip has completely retracted.

While holding trocar tube subassembly 212 in place, the trocar body subassembly 210 is manually removed in a proximal direction as seen in FIG. 11. In this position, the flap valve mechanism (not shown) will close as visually indicated by the position of actuating lever 320 being in a transverse position. In this operation, once the tip 240 of stylet 236 clears the opening 300 in grommet-like seal 294, spring 318 will bias flapper pad 312 into contact with the grommet-like seal, as best seen in FIG. 14B. In this manner, opening 300 will be closed and sealed. Gas pressure in the body cavity is thus maintained. In this regard, the stopcock 326 will normally be closed during trocar insertion to maintain the gas pressure within the body cavity. If necessary, the stopcock may be used as a conduit for admitting an additional insufflating gas into the cavity.

After the trocar body subassembly 214 has been separated from the trocar tube subassembly 212, surgical instruments may be inserted into the body cavity by way of the trocar tube subassembly to view internal tissues, perform operations, and/or drain body fluids. Actuating lever 320 can be used to manually open valve 302 to facilitate such procedures and also permit removal of specimens, as well as to deflate the body cavity.

It is to be understood that while the invention has been described above in conjunction with the preferred specific embodiments, the description and examples are intended to illustrate and not limit the scope of the invention, which is defined by the scope of the appended claims.

What is claimed is:

1. A trocar assembly comprising:

a trocar body including an elongated trocar obturator defining a longitudinal axis and having a piercing tip at a distal end, and including a housing at a proximal end;

an elongated trocar tube defining a longitudinal axis, said tube and obturator being co-axial and said tube having a distal open end and fixed in a position along said longitudinal axis relative to said housing;

manually-actuable extension means within said housing for extending said obturator relative to said tube from a retracted position wherein said tip is recessed from said open end of said tube to a first extended position wherein said tip is extended from said tube end;

latching means within the housing for latching the obturator in the first extended position when no force is applied to the tip of the obturator and unlatches when the obturator moves proximally to a second trocar extended position in response to a force applied to the obturator tip;

restraining means within the housing and separate from the latching means for maintaining the obturator in the second trocar extended position when the latching means unlatches and for thereafter allowing the obturator to return to the retracted position when the force applied to the obturator tip decreases below a threshold level resulting in distal movement of the obturator to said first extended position;

means for controlling the threshold level; and retraction means within the housing for retracting the obturator to the retracted position when the obturator returns to said first extended position.

2. A trocar assembly as recited in claim 1 wherein said manually-actuable extension means includes a pushbutton operatively connected to a proximal end of the obturator and reciprocally mounted to the housing.

3. A trocar assembly as recited in claim 2 further including mechanical advantage means associated with the pushbutton for advancing the obturator a greater distance than the distance advanced by the pushbutton.

4. A trocar assembly as recited in claim 1 wherein said manually-actuable extension means includes lever means operatively connected to the obturator and reciprocally mounted to the housing for advancing the obturator from the first position to the second position.

5. A trocar assembly as recited in claim 1 wherein the retraction means includes biasing means for applying a retraction force on the obturator.

6. A trocar assembly as recited in claim 5 wherein said biasing means includes a torsion spring.

7. A trocar assembly as recited in claim 1 wherein said trocar tube includes a tube body mounted on the proximal end of said trocar tube, means defining an opening in said tube body for admitting said trocar, flap valve means in said tube body normally closing off said opening when said trocar is not admitted into said tube body, wherein said obturator is of generally cylindrical configuration defining a first diameter and having a reduced diameter shank portion at its proximal end, said flap valve means being located so as to be in contact with said shank portion when said obturator is fully admitted in said tube body, said shank portion being of a diameter substantially less than the diameter of said obturator so as to minimize frictional drag on said obturator caused from contact by said flap valve means.

8. A trocar assembly as recited in claim 1 further including a circular seal mounted to a proximal end of the trocar tube and having an aperture therethrough, and wherein said obturator is generally cylindrical defining a first diameter and having a reduced diameter shank portion at its proximal end, said aperture being circular and having a diameter less than that of said first diameter and greater than that of said reduced diameter so that there is no frictional drag on said obturator from said seal when said obturator is in the second position.

* * * * *